United States Patent [19]
Loubier

[11] Patent Number: 5,186,191
[45] Date of Patent: Feb. 16, 1993

[54] MOTOR DRIVEN DENTAL FLOSS APPLICATOR

[76] Inventor: Robert J. Loubier, CR 700E, Box 216K, Roanoke, Ind. 46783

[21] Appl. No.: 784,983

[22] Filed: Oct. 30, 1991

[51] Int. Cl.⁵ .......................................... A61C 15/00
[52] U.S. Cl. .................... 132/322; 132/324; 132/325
[58] Field of Search ............ 132/322, 323, 324, 325, 132/326

[56] References Cited

U.S. PATENT DOCUMENTS

| | | | |
|---|---|---|---|
| 3,667,483 | 6/1972 | McCabe | 132/322 |
| 3,734,107 | 5/1973 | Thierman | 132/325 |
| 4,151,851 | 5/1979 | Bragg | 132/326 |
| 4,214,598 | 7/1980 | Lee | 132/325 |
| 4,508,125 | 4/1985 | Loubier | 132/326 |
| 4,706,695 | 11/1987 | Urso | 132/322 |

FOREIGN PATENT DOCUMENTS 2141935  1/1985  United Kingdom ............... 132/325

Primary Examiner—Cary E. O'Connor
Attorney, Agent, or Firm—Barnes & Thornburg

[57] ABSTRACT

A motor driven dental floss applicator for use in dispensing and supporting a strand of dental floss for cleaning teeth comprising a rigid elongated frame having a handle on one end and two laterally spaced, upstanding furcations on the other end, the furcations having floss-guiding portions on the tips thereof by means of which a floss strand may be tensioned and moved therebetween. A supply of strand is supported on the frame. A supply and takeup device is provided for supplying and taking up the strand after it is threaded across the tips of the furcations. An electric motor is provided on the frame for actuating the second means unidirectionally, and a switch is provided for controlling the energization of the motor whereby the strand may be controllably drawn across and between said furcations.

12 Claims, 2 Drawing Sheets

MOTOR DRIVEN DENTAL FLOSS APPLICATOR

BACKGROUND OF THE INVENTION

1. Field of the Invention

The relates to dental floss applicators for use in dispensing and supporting a strand of dental floss under tension for cleaning the teeth, and more particularly to an applicator provided with an electric motor for unidirectionally moving the floss strand at a slow speed while the applicator is being used.

II. Description of the Prior Art

The present invention is an improvement over the prior art as disclosed in the following listed U.S. Pat. Nos.: 3,759,274; 3,847,167; 4,214,598; 4,245,658; 4,508,125; 4,512,354; and Des. No. 375,439

SUMMARY OF THE INVENTION

The present invention constitutes an improvement over the aforesaid prior art patents in the respect of motorizing the applicator such that the floss strand may be moved continuously unidirectionally to carry away foreign matter and debris during the flossing operation. Power is provided preferably by means of an electric, D.C. motor which may be energized intermittently as the user may prefer.

More particularly, the invention comprises a motor driven dental floss applicator for use in dispensing and supporting a strand of dental floss for cleaning teeth comprising an elongated supporting frame having on one end two laterally spaced furcations. The furcations have floss-guiding portions on the tips thereof by means of which a floss strand may be tensioned and moved therebetween. A handle portion is provided on the other end of the frame. A cylindrically shaped capstan device is mounted for rotation on the frame with supply and takeup portions axially spaced thereon. The axis of the capstan extends transversely to the longitudinal axis of the frame. The capstan supply and takeup portions are on opposite sides, respectively, of the frame and the frame is provided with a supply of floss strand therein and means for resisting tensing movement of the strand therefrom. The strand is threaded about the supply capstan, across the furcations, and about the takeup capstan, this threading being in a direction that, as the capstan is rotated in one direction, the strand is tensed from the supply portion, across the furcations and about the takeup portion. An electric motor means is mounted on the handle for imparting rotation to the capstan in only one direction, and means for controlling the energization of the motor means is provided whereby the strand may be controllably drawn across and between the furcations.

It is an object of this invention to provide an improved dental floss applicator.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF THE PREFERRED EMBODIMENT

Figure 1:
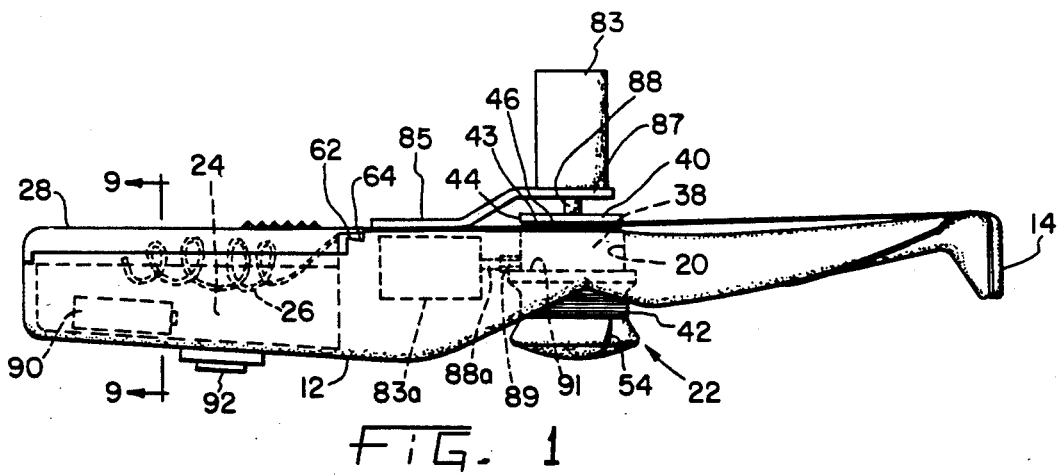
FIG. 1 is a side view of an embodiment of this invention.

Referring to the drawings, the applicator is constructed insofar as the frame is concerned essentially like that disclosed in U.S. Pat. No. 4,508,125. The applicator comprises an elongated, rigid body 12 formed of a suitable plastic material such as high density polyethylene. It is shaped as shown, being provided with rounded corners and edges on all parts so as to avoid chafing of the dental floss and to facilitate manipulation. Molded integrally onto one end of the body 12 are furcations 14 and 16 which are generally parallel and spaced apart laterally of the body 12. The adjacent portion of the body 12 is necked down as shown and widened at the end to provide a bridge portion 18 from which the furcations 14 and 16 extend.

About midway between the ends, the body 12 is provided with a cylindrical bearing opening 20 which frictionally receives for rotation a capstan device indicated generally by the numeral 22.

To the left side of the capstan device 22 as viewed in FIG. 1, the body 12 is provided with an elongated cavity or chamber 24 which receives a supply of floss strand 26 either in loose or spool form. A plastic cap 28 is slidably secured to the body 12 over the elongated opening 30 of chamber 24 which will be explained in more detail later on.

The capstan device 22 is a one-piece element preferably molded, made of material hard enough to withstand the compression of the floss under tension. Delrin (Dupont trademark for acetal plastic) is an appropriate material. Between the end portions, the capstan device 22 is provided with a journal bearing portion 38 which frictionally fits into the bearing opening 20. On one end is a supply capstan portion 40 and on the other end a takeup capstan portion 42. It will be noted that both portions 40 and 42 project beyond the adjacent sides of the body 12 as shown.

Preferably, the axis of the capstan device 22 is canted slightly with respect to the longitudinal axis of the body 12. The supply capstan 40 is of a diameter no larger than the journal bearing 38 so that the capstan device 22 may be easily inserted into the bearing opening 20 and removed as desired.

The portion 40 is composed of two flanges 43 and 44 and a cylindrical barrel portion 46.

Figure 9:
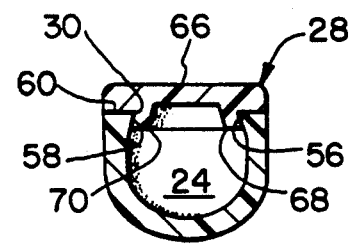
FIG. 9 is a cross-section taken substantially along section line 9—9 of FIG. 1.
Figure 6:
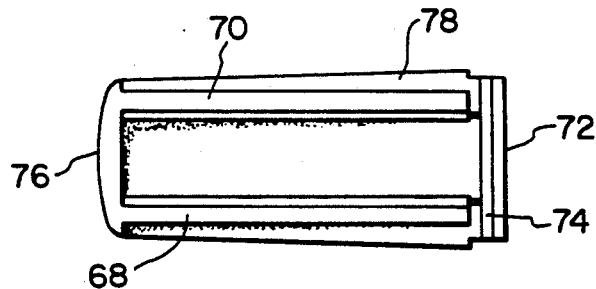
FIG. 6 is a plan view of the underside of the cover.
Figure 7:
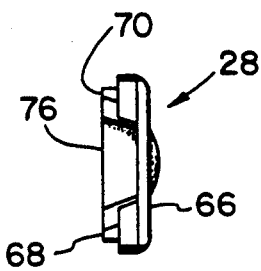
FIG. 7 is an end view thereof.
Figure 8:
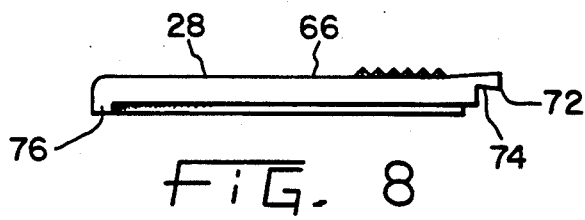
FIG. 8 is a side view thereof.

The chamber 24 is elongated and defined in part by two wall surface portions 56 and 58 which are elongated, spaced apart and generally parallel, and further are angled inwardly toward each other as shown in FIG. 9. The opening 30 further has a coplanar, flat rim portion 60. The wall surface portions 56 and 58 can jointly serve as an elongated guideway as will be explained in more detail later on. Adjacent to the capstan device 22, and just ahead of the opening 30, the frame 12 is provided with two transversely extending, elongated, raised and recessed portions 62 and 64 which cooperate with similarly shaped portions on the cover 28 for detachably securing the latter in closed position over the chamber opening 30.

The cover 28 has an essentially flat top 66 and is provided on the underside with two elongated, spaced apart and parallel, rail-like elements 68 and 70 having outer surfaces shaped to complement the wall surface portions 56 and 58 so as to be slidably engageable therewith. At the forward end of the cover 28 there is provided elongated, transversely extending raised and recessed portions 72 and 74 shaped to have a snap or detent-type fit with the recessed and raised portions, respectively, 64 and 62 on the body 12. The cover 28 is adapted to have a sliding fit in the guideway 56, 58 until the detent portion 72, 74 engages and snaps over and into mating relation with the detent portion 62, 64 on the body 12. The cover 28 is thereupon locked in place against rearward movement. Outward or lateral movement of the cover 28 is resisted by the wedge-type engagement of the guide elements 68 and 70 in the guideway 56 and 58. The aft end of the handle 12 is closed by engagement of the depending flange 76 on the cover 28 which fits into a companion notch in the frame 12 when the detent means 62, 64, 72, 74 is engaged.

The underside of the cover 28 laterally outwardly of the two elongated guide elements 68 and 70 as indicated by the numeral 78 is flat and coplanar and thereby slidably engageable with the upper flat surface 60 on the frame 12, which surrounds the chamber opening 30. Thus, the cover 28 may be slidably reciprocated along the open side of the chamber 24 into closed and opened positions as desired.

Figure 2:
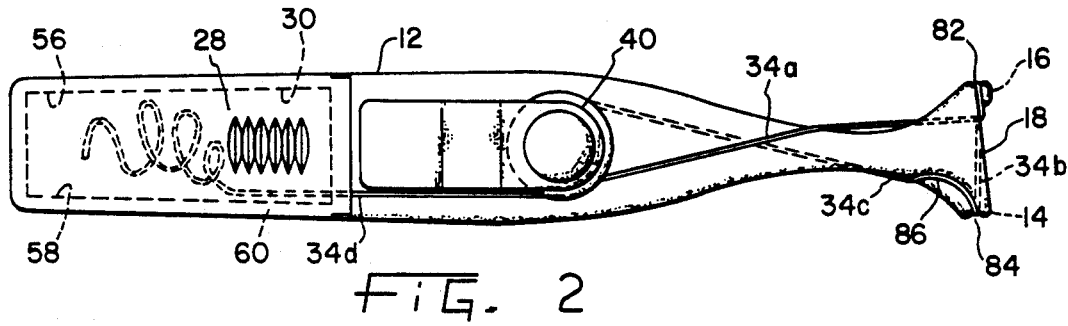
FIG. 2 is a top view thereof.
Figure 3:
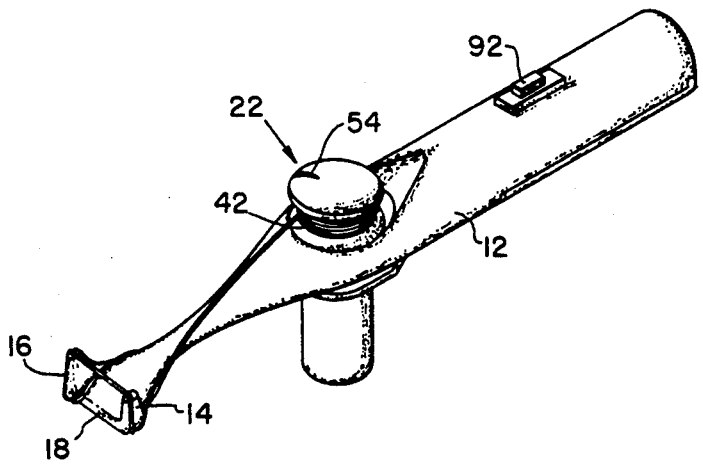
FIG. 3 is a perspective view.
Figure 4:
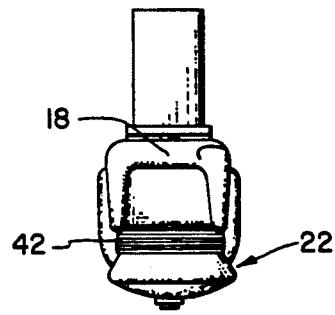
FIG. 4 is an end view.

The floss strand 26 is threaded on the applicator with the cover 28 slightly ajar. The strand is wrapped two or three turns around the supply capstan portion 46 counterclockwise as shown in FIG. 2, from there along the body 12 to the furcation 16, the strand portion 34a passing on the inside of the furcation 16 around and through the groove 82 and across the span to the furcation 14. Here the strand portion 34b passes through the groove 84 alongside the furcation 14, through the groove 86 at the butt portion to a position of section 34c. The section 34c then extends to and wraps around the barrel section 42 of the takeup capstan portion counterclockwise again as viewed in FIG. 2, two or more turns, the end then being forced into the groove 54 which retains the strand in place.

After threading, the cover 28 is slid in the guideway 56, 58 forwardly until the detent portions 62, 64, 72, 74 snap into engagement which thereupon holds the cover 28 in closed position. Prior to snapping the cover 28 in position, it will be noted that the strand 26 overlies the detent portion 62, 64 on the frame 12 such that when the cover 28 is snapped into place, the strand in the region indicated by the numeral 34d is frictionally clamped or gripped between the detent portion 62, 64 on the frame 12 and the corresponding detent portion 74, 72 on the cover 28. This frictional gripping resists withdrawal of the strand 26 from the chamber 30.

The device thus far described and illustrated is like that disclosed in U.S. Pat. No. 4,508,125.

An electric motor 83 of the direct current type is suitably mounted on the frame 12 and operatively connected to the capstan device 22. As shown more clearly in FIG. 1, a bracket 85 is suitably secured to the surface of the frame 12 just ahead of the cover 28 and has a raised portion 87 which mounts directly the motor 83. The rotatable shaft 88 of the motor 83 is coaxially secured to the capstan device 22 such that when the motor 83 is energized, the capstan device 22 will be correspondingly rotated.

Figure 5:
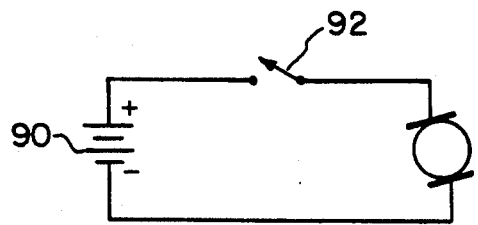
FIG. 5 is an electrical diagram of a suitable circuit which may be used for controlling the energization of the electric motor.

The motor has energizing circuitry connected thereto as diagrammatically shown in FIG. 5, this circuitry including a suitable battery 90 and a normally open, manually operable switch 92. Upon closure of the switch 92, the motor 83 will be energized.

In the operation of the applicator, the switch 92 is closed causing the motor 83 to be energized. The capstan 22 is rotated until the floss-strand across the furcations 14 and 16 is suitably tensioned. The floss is then used in the typical matter by inserting the section 34b between the teeth. The capstan 22 is rotated very slowly by the motor 83 so as to present a new section 34b of floss as the user proceeds with the cleaning operation. Thus, the debris and foreign matter collected between the teeth is continuously being carried away by the floss as new floss is being presented. As just explained, this movement of the floss is continuous and at a suitably slow speed.

Another embodiment of the motorized version of this applicator is shown in dashed lines in Figure with the same reference numerals identifying the equivalent parts with the alternative parts being further identified by the suffix letter "a."

The electric motor is mounted internally of the chamber 30 and carries on the outboard end of the shaft 88a a small spur gear 89. This spur gear is meshed with a ring gear 91 which is coaxially secured to the barrel of the capstan device 22. Thus, when the motor 83a energized, the shaft 88a is rotated causing the ring gear 91 as well as the capstan device 22 to rotate.

It is to be emphasized that it is important that the electric motor rotate in one direction only and essentially continuously so long as the user is cleaning his or her teeth. The switch 92 is conveniently positioned on the frame 12 such that the user may manipulate it to turn the motor "on" and "off" as desired.

The present invention is to be contrasted with the prior art, motorized versions wherein the motor mechanism is so arranged as to cause the floss strand to reciprocate or oscillate to cause the strand to move back and forth between the teeth. This reciprocation is deliberately avoided in the present invention, since it is desired to present a clean segment of the floss continuously and also continuously to carry away debris and foreign matter which may be collected between the teeth.

Typical of the prior art as to which the floss strand is reciprocated are U.S. Pat. Nos. 3,759,274; 3,847,167; and 4,245,658.

While there have been described above the principles of this invention in connection with specific apparatus, it is to be clearly understood that this description is made only by way of example and not as a limitation to the scope of the invention.

What is claimed is:

1. A motor driven dental floss applicator for use in dispensing and supporting a strand of dental floss for cleaning teeth comprising:
   a rigid elongated supporting frame having on one end two laterally spaced furcations, said furcations having floss-guiding portions on the tips thereof by means of which a floss strand may be tensioned and moved therebetween, said frame having a handle portion on its other end,
   first means for storing floss strand on said frame, second means for supplying and taking-up said strand after it is threaded across the tips of said furcations, and electric motor means for actuating said second means unidirectionally, and means for controlling energization of said motor means whereby said strand may be controllably drawn across and between said furcations, wherein said motor means is rigidly and stationarily mounted to said frame, and wherein said motor means, said handle and said furcations are relatively rigidly and stationarily disposed such that, when the motor means is energized, the strand moves in a single, axially directed motion relative to the motor means, the handle and the furcations.

2. The applicator of claim 1 wherein said second means includes a cylindrically shaped capstan device mounted for rotation on said frame with supply and takeup portions axially spaced thereon, the axis of said capstan extending transversely to the longitudinal axis of said frame, said supply and takeup portions being on opposite sides, respectively, of said frame, said first means includes a supply of floss strand and means for resisting movement of said strand, said strand being threaded about said supply capstan portion, across said furcations, and about said takeup capstan portion, said threading being in a direction that as said capstan is rotated in one direction said strand is tensed from said supply portion, across said furcations and about said takeup portion, said motor means being mounted to impart rotation to said capstan in only said one direction.

3. A motor driven dental floss applicator for use in dispensing and supporting a strand of dental floss for cleaning teeth comprising:

a rigid elongated supporting frame having on one end two laterally spaced furcations, said furcations having floss-guiding portions on the tips thereof by means of which a floss strand may be tensioned and moved therebetween, a handle portion on the other end of said frame;

first means for storing floss strand on said frame;

second means for supplying and taking-up said strand after it is threaded across the tips of said furcations; and electric motor means mounted on said frame for actuating said second means unidirectionally, and means for controlling energization of said motor means whereby said strand may be controllably drawn across and between said furcations;

wherein said second means includes a cylindrically shaped capstan device mounted for rotation on said frame with supply and takeup portions axially spaced thereon, the axis of said capstan extending transversely to the longitudinal axis of said frame, said supply and takeup portions being on opposite sides, respectively, of said frame; and wherein said first means includes a supply of floss strand and means for resisting movement of said strand, said strand being threaded about said supply capstan portion, across said furcations, and about said takeup capstan portion, said threading being in a direction that as said capstan is rotated in one direction said strand is tensed from said supply portion, across said furcations and about said takeup portion, said motor means being mounted to impart rotation to said capstan in only said one direction; and wherein said motor means includes a bracket secured to said frame, a slow-speed motor unit mounted on said bracket and having a shaft coaxially secured to said capstan to impart rotation thereto, said means for controlling energization including an electrical switch which may be closed for energizing continuously said motor unit and for moving said strand unidirectionally continuously between said furcations.

4. A motor driven dental floss applicator for use in dispensing and supporting a strand of dental floss for cleaning teeth comprising:

a rigid elongated supporting frame having on one end two laterally spaced furcations, said furcations having floss-guided portions on the tips thereof by means of which a floss strand may be tensioned and moved therebetween, a handle portion on the other end of said frame;

first means for storing floss strand on said frame;

second means for supplying and taking-up said strand after it is threaded across the tips of said furcations; and electric motor means mounted on said frame for actuating said second means unidirectionally, and means for controlling energization of said motor means whereby said strand may be controllably drawn across and between said furcations;

wherein said second means includes a cylindrically shaped capstan device mounted for rotation on said frame with supply and takeup portions axially spaced thereon, the axis of said capstan extending transversely to the longitudinal axis of said frame, said supply and takeup portions being on opposite sides, respectively, of said frame; and wherein said first means includes a supply of floss strand and means for resisting movement of said strand, said strand being threaded about said supply capstan portion, across said furcations, and about said takeup capstan portion, said threading being in a direction that as said capstan is rotated in one direction said strand is tensed from said supply portion, across said furcations and about said takeup portion, said motor means being mounted to impart rotation to said capstan in only said one direction; and wherein said motor means includes a slow speed motor unit secured internally of said frame, said capstan having a ring gear coaxially secured thereto and disposed internally of said frame, said motor unit having a shaft provided with a spur gear meshed with said ring gear for imparting rotation to said capstan, said means for controlling energization including an electrical switch which may be closed for energizing continuously said motor unit and for moving said strand unidirectionally continuously between said furcations.

5. A motor driven dental floss applicator for use in dispensing and supporting a strand of dental floss for cleaning teeth comprising:

a rigid elongated supporting frame having on one end two laterally spaced furcations, said furcations having floss-guiding portions on the tips thereof by means of which a floss strand may be tensioned and moved therebetween, and said frame having a handle portion on its other end of said frame;

first means for storing floss strand on said frame;

second means for supplying and taking-up said strand after it is threaded across the tips of said furcations; and electric motor means mounted on said frame for actuating said second means unidirectionally, and means for controlling energization of said motor means whereby said strand may be controllably drawn across and between said furcations;

wherein said second means includes a cylindrically-shaped capstan device mounted for rotation on said frame, the axis of said capstan device extending transversely to the longitudinal axis of the frame; and wherein said motor means includes a bracket secured to said frame, and a motor mounted on said bracket and having a shaft coaxially secured to the capstan device to impart rotation thereto.

6. The applicator of claim 5 wherein said capstan device includes axially spaced supply and takeup means, said supply and takeup means being on opposite sides, respectively, of said frame.

7. The applicator of claim 5 wherein said first means includes a supply of floss strand and means for resisting movement of said strand, said strand being threaded about said supply means, across said furcations, and about said takeup means, said threading being in a direction that as the capstan device is rotated in one direction the strand is pulled from said supply means, across said furcations, and about said takeup means.

8. The applicator of claim 5 wherein said motor, when energized, moves the strand continuously and unidirectionally between the furcations.

9. A motor driven dental floss applicator for use in dispensing and supporting a strand of dental floss for cleaning teeth comprising:

a rigid elongated supporting frame having on one end two laterally spaced furcations, said furcations having floss-guiding portions on the tips thereof by means of which a floss strand may be tensioned and moved therebetween, and said frame having a handle portion on its other end of said frame;

first means for storing floss strand on said frame;

second means for supplying and taking-up said strand after it is threaded across the tips of said furcations; and electric motor means mounted on said frame for actuating said second means unidirectionally, and means for controlling energization of said motor means whereby said strand may be controllably drawn across and between said furcations;

wherein said second means includes a cylindrically-shaped capstan device mounted for rotation on said frame, the axis of said capstan device extending transversely to the longitudinal axis of the frame; and wherein said motor means includes a motor secured internally of said frame, said capstan device having a ring gear coaxially secured thereto and disposed internally of said frame, said motor having a shaft provided with a spur gear meshed with said ring gear for imparting rotation to the capstan device.

10. The applicator of claim 9 wherein said capstan device includes axially spaced supply and takeup means, said supply and takeup means being on opposite sides, respectively, of said frame.

11. The applicator of claim 9 wherein said first means includes a supply of floss strand and means for resisting movement of said strand, said strand being threaded about said supply means, across said furcations, and about said takeup means, said threading being in a direction that as the capstan device is rotated in one direction the strand is pulled from said supply means, across said furcations, and about said takeup means.

12. The applicator of claim 9 wherein said motor, when energized, moves the strand continuously and unidirectionally between the furcations.

* * * * *